US006469148B1

(12) United States Patent
Rochlin

(10) Patent No.: US 6,469,148 B1
(45) Date of Patent: Oct. 22, 2002

(54) PROCESS FOR LARGE SCALE PREPARATION OF SPHINGOSINES AND CERAMIDES

(75) Inventor: Elimelech Rochlin, Shimshon (IL)

(73) Assignee: Lipiderm Ltd., Jerusalem (IL)

( * ) Notice: Subject to any disclaimer, the term of this patent is extended or adjusted under 35 U.S.C. 154(b) by 0 days.

(21) Appl. No.: 09/568,387

(22) Filed: May 10, 2000

Related U.S. Application Data

(60) Provisional application No. 60/133,526, filed on May 10, 1999.

(51) Int. Cl.[7] ............................................... C07H 15/00
(52) U.S. Cl. ........................................ 536/18.6; 554/78
(58) Field of Search ............................ 554/78; 564/427, 564/507, 489, 476; 449/371, 372, 434; 536/18.6

(56) References Cited

U.S. PATENT DOCUMENTS 4,937,328 A * 6/1990 Schmidt et al. ................ 536/18
5,110,987 A    5/1992 Liotta et al.

OTHER PUBLICATIONS

Schmidt et al, Synthisis of Sphingosines. 4. Synthesis of erythrosphingosines via their azido derivatives, Tetrahedron Letters, 1988, vol. 7, 663–7, see abs AN 1988:473824.*

Schmidt et al, Synthesis of phingosines, Pt. 2 Synthesis d–erythro=sphingosines, Tetrahedron Letters 1986, vol. 27 iss 4, 481–484, see abs, AN 1986:460459.*

Ohashi, et al., Synthesis of D–Erythro–1–Deoxydihydroceramide–1–Sulfonic Acid, Tetrahedron Letters, 1988; 29(10): 1185–1188.

Schiemenz, et al., Aromatic Phosphines with Second–Order Substituents, III[2]: A New Variant on the Wittig Reaction, Chem. Ber., 1966; 99: 2663–2668.

Polt, et al., Aluminoxy Acetals from α–Amino Esters: Chirality Transfer via Sequential Addition of Hydride and C–Nucleophiles. 2–Amino Alcohols and Sphingosines, J. Org. Chem., 1992; 57: 5469–5480.

Kiso, et al., A Novel Route to D–erythro–Sphingosine and Related Compounds from Mono–O–Isopropylidene–D–Xylose or D–Galactose, Carbohydrate Research, 1986; 158: 101–111.

Imokawa, et al., Water–retaining Function in the Stratum Corneum and Its Recovery Properties by Synthetic Pseudoceramides, J. Soc. Cosmet. Chem., 1989; 40: 273–285.

Kerscher, et al., Skin Ceramides: Structure and Function, European Journal of Dermatology, 1991; 1: 39–43.

Herold, Synthesis of D–erythro–and D–threo–Spingosine Derivatives from L–Serine, Helvelica Chemica Acta, 1988; 71: 354–362.

Gros, et al., Reaction of Ammonia with Some Acetylated and Benzoylated Monosaccharides. IX. The Migration of Benzoyl Groups in the Ammonolysis of 1,2,3,4,6–PentaO–benzoyl–D–galactoses, J. Org. Chem., 1964; 29: 3647–3654.

Zimmermann, et al., Synthese von erythro–Sphingosinen uber die Azidoderivate, Liebigs Ann. Chem., 1988; 663–667.

* cited by examiner

*Primary Examiner*—Deborah Carr
(74) *Attorney, Agent, or Firm*—Browdy and Neimark

(57) ABSTRACT

Synthetic methods for convenient large scale preparation of D-erythro sphingosines and ceramides of high isomeric purity are described.

5 Claims, 3 Drawing Sheets

PROCESS FOR LARGE SCALE PREPARATION OF SPHINGOSINES AND CERAMIDES

This application claims priority to U.S. provisional application Ser. No. 60/133,526, filed May 10, 1999, which is hereby incorporated by reference in its entirety.

FIELD OF THE INVENTION

The present invention relates to synthetic methods for the preparation of D-erythro sphingosines and ceramides of high isomeric purity, and in particular to methods suitable for large scale production.

REFERENCES

Gros, E. G. and Deulofeu, V., *J. Org. Chem.* 29:3647–54 (1964).
Herold, *Helv. Chim. Acta* 71:354 (1988).
Kerscher, M. et al., *Eur. J. Derinatol.* 1:39–43 (1991)
Imokawa, G. et al., *J. Soc. Cosmet. Chem.* 40:273–285 (1989).
Kiso, M. et al., *Carbohydrate Research* 158:101–111 (1986).
Liotta, D. and Merrill, A. H., U.S. Pat. No. 5,110,987 (1992).
Polt et al., *J. Org. Chem.* 57:5469 (1992).
Schiemenz, G. P. and Thobe, *J., Chem. Ber.* 99:2263 (1966).
Schmidt, R. R. and Zimmerman, P., *Tetrahedron Lett.* 27(4): 481–86 (1986).
Schmidt, R. R. and Zimmerman, P., *Liebigs Ann. Chem.* 663–667 (1988).
Schmidt, R. R. and Zimmerman, P., U.S. Pat. No. 4,937,328 (1990).

BACKGROUND OF THE INVENTION

Sphingosines constitute a group of related long-chain aliphatic 2-amino-1,3-diols, of which Derythro-1,3-dihydroxy-2-amamino-1,3-diols, of which D-erythro-1,3-dihydroxy-2-amino-4,5-trans-octadecene is the most frequently occurring in animal tissues. N-acylsphingosines are also referred to as ceramides. Sphingosines, ceramides, and their glycosides, glycosphingolipids, are of great interest because of their diverse bioactivities and biological roles. These activities include inhibition of protein kinase C activity and transfer of information between developing vertebrate cells. Sphingosines also serve as chain terminators in various gangliosides. Galactosyl ceramide has been shown to be a receptor for HIV binding in cells lacking the CD4 receptor.

Skin ceramides are also believed to play an important role in the water permeability properties of the skin, providing an epidermal water barrier which strengthens the skin structure and reduces water loss. Ceramides and synthetic analogs have thus been used as components of skin care compositions, and have been found effective in restoring the water content of dry skin and in relieving atopic eczema (Kerscher et al.; Imokawa et al.).

These compounds have proven difficult to extract from natural sources, where they are present in low concentrations. Chemical synthetic methods reported to date have generally been laborious and expensive. Several reported methods of synthesizing optically pure sphingosines and their derivatives rely on the use of serine as a chiral building block. See, for example, Polt et al., Herold, and U.S. Pat. No. 5,110,987. However, methods utilizing serine as a starting material are quite lengthy and thus are not amenable to potential scale-up. Other synthetic approaches to the preparation of isomerically pure sphingosines and ceramides have employed other chiral starting materials, such as carbohydrates, L-glyceric and D-tartaric acids, and/or asymmetric reactions. Although successful as gram-scale procedures, these strategies generally fail or become prohibitively expensive when applied to kilogram scale processes. Enzymatic methods of synthesis have also been described but are often unpredictable, giving varying results depending on medium or the particular enzyme preparation.

Accordingly, a reliable, convenient and versatile method of large scale preparation of these compounds is desirable.

SUMMARY OF THE INVENTION

The present invention includes, in one aspect, a convenient process for the large scale preparation of sphingosine, a sphingosine analog, or a ceramide. The process comprises the following series of steps. A stirred slurry of benzaldehyde and a Lewis acid, preferably $ZnCl_2$, is formed and contacted with D-galactose, with continued stirring. The resulting mixture is filtered to obtain a solid precipitate and a filtrate. The filtrate is then diluted with a mixture of diethyl ether and a hydrocarbon solvent, preferably a paraffinic solvent such as hexane, ligroin, or, more preferably, petroleum ether, typically in approximately equal proportions. The resulting mixture is extracted with cold water to provide an aqueous extract, which is treated with a base, such as an alkaline or alkaline earth carbonate or bicarbonate, to produce a precipitate of zinc salts. This precipitate is removed to provide an aqueous solution of 4,6-O-benzylidene-D-galactose. Alternatively, the zinc cation may be removed by treatment with an ion exchange resin. The resulting solution is then treated, preferably without isolation, with an oxidizing agent, preferably sodium periodate, which oxidatively cleaves the 4,6-O-benzylidene-D-galactose, to produce the protected hydroxy aldehyde, 2,4-O-benzylidene-D-threose. This compound is then reacted with a Wittig reagent, e.g. $(Ar)_2P=CHR$, where Ar is aryl and R is a $C_4$–$C_{26}$ branched or unbranched alkyl or alkenyl chain, to produce a hydroxy olefin.

The hydroxyl group of the resulting hydroxy olefin is then converted to a suitable leaving group, such as a tosylate, mesylate, or trifluoromethanesulfonate. Preferably, the hydroxy olefin is reacted with a tritlating agent, such as trifluoromethyl sulfonic anhydride. Subsequent reaction with sodium azide, followed by a hydride reducing agent, such as $LiAlH_4$ or $NaBH_4$, produces an amino olefin. Finally, this compound is deprotected (i.e. the benzylidene group is removed) by contacting it with an acidic ion exchange resin, to produce sphingosine (where R is n-$C_{13}H_{27}$, tridecyl) or a sphingosine analog (where R is a longer or shorter alkyl chain, e.g. $C_4$–$C_{12}$ or $C_{14}$–$C_{26}$).

Alternatively, for the production of ceramides, the amino olefin is acylated, by treating with a $C_2$–$C_{26}$ acylating agent, such as an acyl halide, anhydride, or carboxylic acid, in the presence of any necessary acylating catalyst, prior to the deprotection step.

The invention also provides convenient large scale processes for the production of two of the intermediates, i.e. 4,6-O-benzylidene-D-galactose and 2,4-O-benzylidene-D-threose, by carrying out the process described above up to the oxidative cleavage step, or through the oxidative cleavage step, respectively. D-threose may also be obtained in large quantities by deprotection of the intermediate, 2,4-O-benzylidene-D-threose.

These and other objects and features of the invention will become more fully apparent when the following detailed

DETAILED DESCRIPTION OF THE INVENTION

The process described herein, suitable for large scale production of sphingosines and ceramides, is based in part on the preparation of 1,3-O-benzylidene-2-azido-(D-erythro-sphingosine) (5) from D-galactose (1) as reported by Schmidt and Zimmerman (1986, 1988,1990) and the sphingosine and ceramide preparations reported by Kiso et al. (1986). However, the present process incorporates significant modifications, resulting in substantial reductions in expenditure of time and labor. As used herein, "large scale" refers to kilogram, preferably multikilogram, quantities. The term "sphingosines" includes sphingosine itself and analogs which have the basic structure of sphingosine but vary in the length of the fatty alkyl chain.

Figure 1:
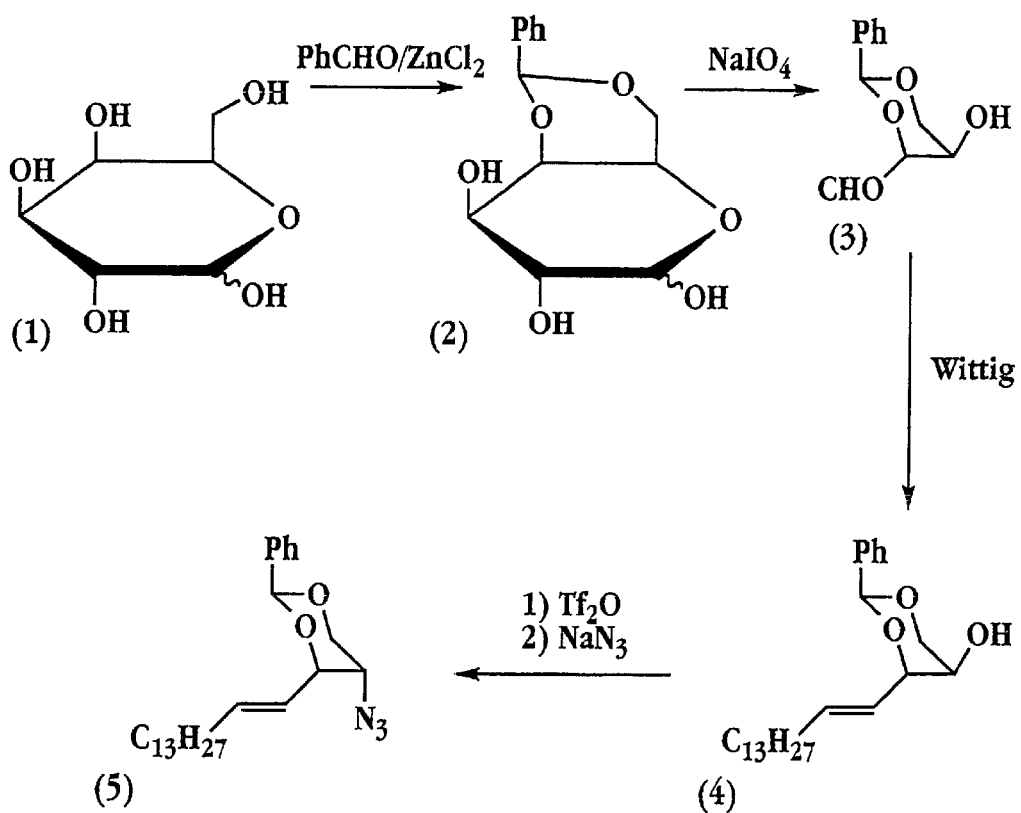
FIG. 1 shows a synthetic scheme for the large scale preparation of 1,3-O-benzylidene-2-azido-(D-erythro-sphingosine) (5) from D-galactose (1)
Figure 2:
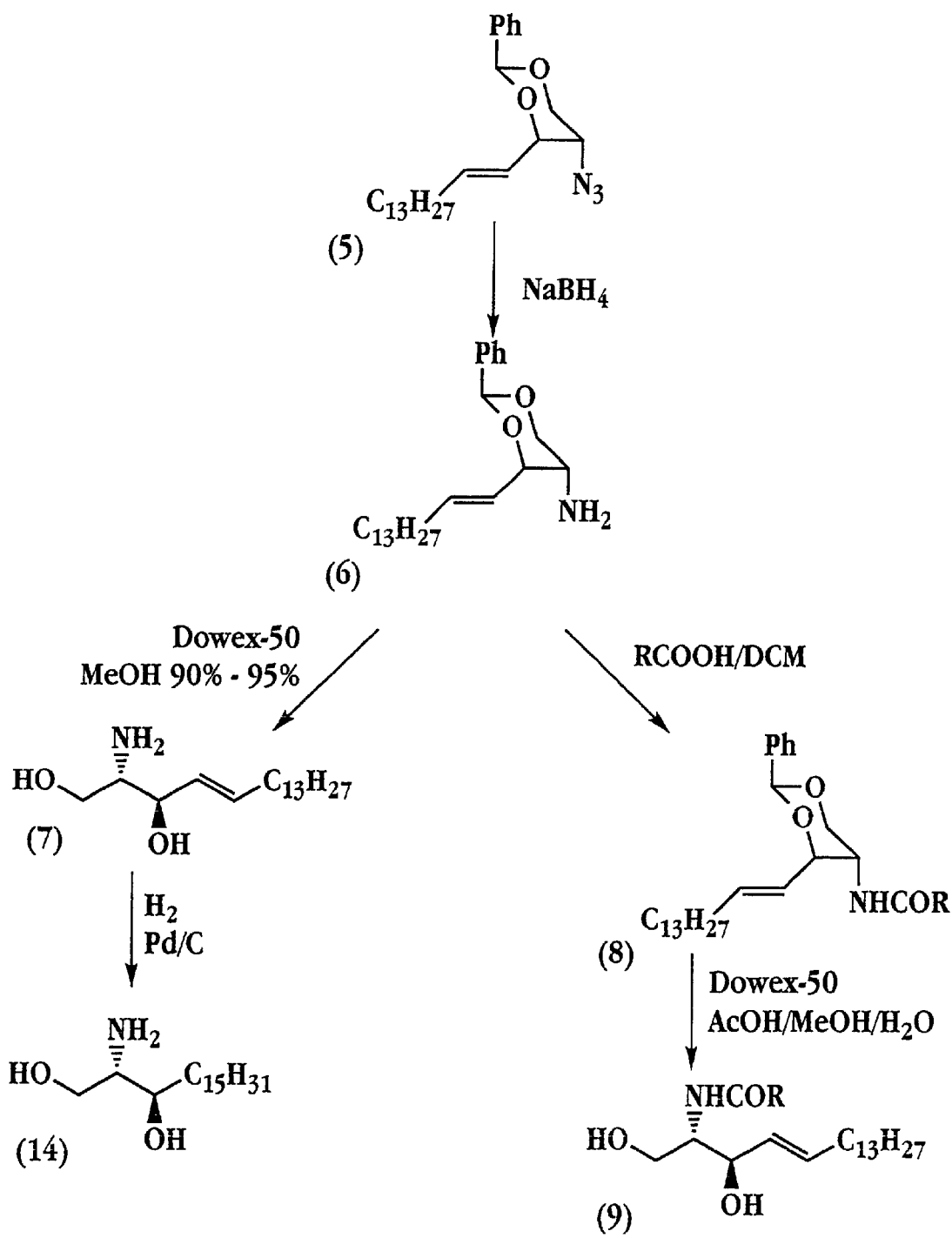
FIG. 2 shows a synthetic scheme for the large scale preparation of sphingosine (7), dihydrosphingosine (14), and a ceramide (9) from the intermediate (5)
Figure 3:
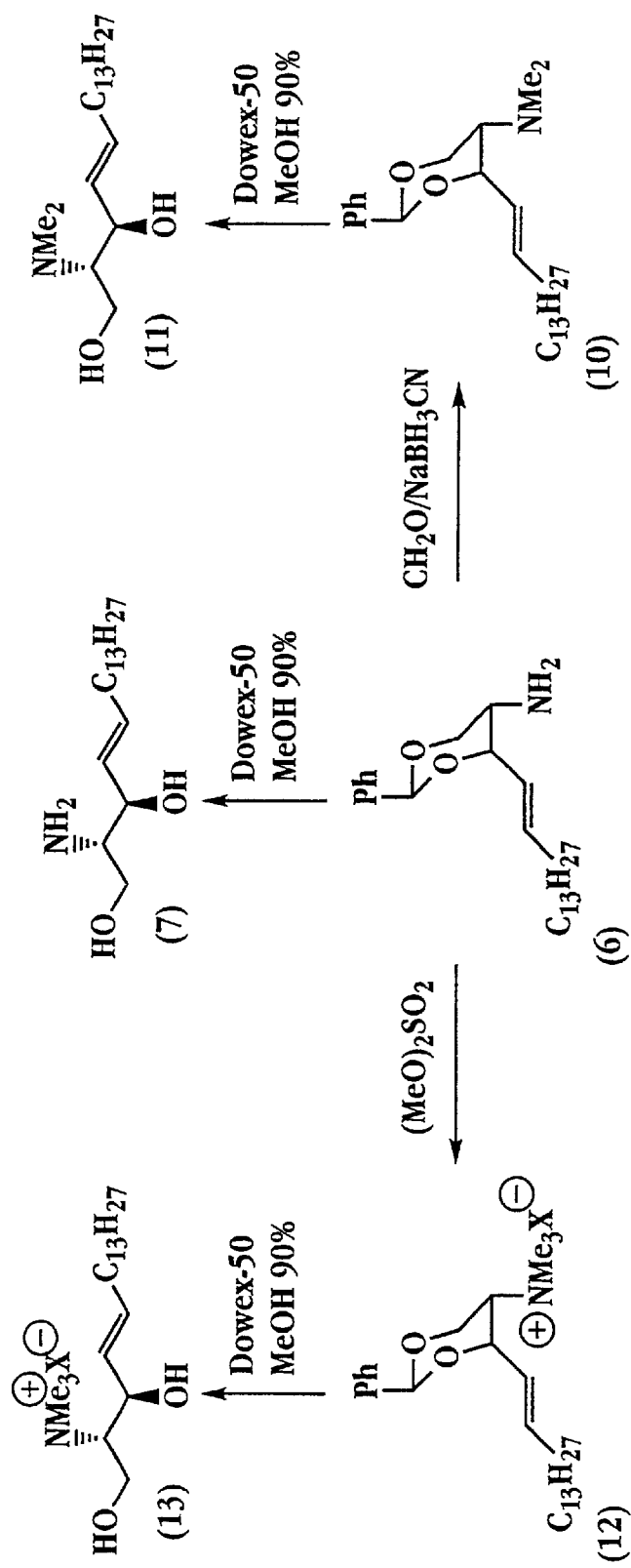
FIG. 3 shows a synthetic scheme for the large scale preparation of N-alkylated sphingosines.

As shown in FIGS. 1–3, the process may be used for the production of derivatives such as dihydrosphingosines, N,N-dimethyl- and N,N,N-trimethyl sphingosines, and ceramides having fatty acid components of various lengths. The process can also be modified for the preparation of phosphoand glycosphingolipids. The individual steps of the process will now be described.

A. Benzvlidenation of D-Qalactose

The procedure followed by Schmidt and Zimmerman is based on that reported by Gros and Deulofeu (1964). The product, 4,6-O-benzylidene-D-galactose (BG) and 1,2,3,4-0-dibenzylidene-D-galactose. The products was isolated by a time- and labor-intensive procedure which included the following steps:

1. Decomposition of the reaction mixture in water,
2. Slow (overnight) separation of organic and aqueous phases at 5° C.,
3. Washing of the organic phase with water,
4. Neutralization and $ZnCO_3$ precipitation from the combined aqueous solution,
5. Filtration of $ZnCO_3$ and washing of the filter with additional water,
6. Evaporation of the resulting aqueous solution to dryness in vacuo at ~40–45° C.,
7. Extraction of the solid residue with boiling ethyl acetate to separate the 4,6-O-benzylidene galactose (BG) from unreacted galactose and salts, and
8. Concentration of resulting ethyl acetate solution and crystallization of BG (2).

Stages of this procedure which are likely to be problematic for scaleup include the extended phase separation (step 2), during which the product is exposed to low pH, the extended evaporation (step 6), and the prolonged extraction of the solid residue with hot ethyl acetate (step 7). The quality of extraction may depend very much on the purity of the ethyl acetate. In some cases, the prolonged hot ethyl acetate exposure causes caramelization of galactose-BG-salt mixture and prevents complete extraction of the product.

In accordance with the present invention, the procedure was modified to overcome these problems, based in part on the following observations made by the inventors:

(1.) The undissolved residue remaining in the reaction mixture following the benzylidenation is not $ZnCl_2$ as previously reported (Gros and Deulofeu), but unreacted D-galactose. When this residue was filtered off, no D-galactose was detected by TLC in the reaction mixture. Therefore, the unreacted D-galactose can be separated from the product by simple filtration of the reaction mixture prior to its decomposition by water, rather than by later extraction of the product with a hot solvent.

(2.) The phase separation after decomposition of the reaction mixture by water is accelerated by addition of an ether/hydrocarbon (preferably ether/petroleum ether) mixture.

(3.) After the aqueous phase is neutralized by $K_2CO_3$ or ($Na_2CO_3$), and $ZnCO_3$ is filtered off (or, alternatively, $Zn^{2+}$, cations are removed by ion-exchange resin IRC-50S), an aqueous solution of BG and salts (KCl or NaCl) is obtained. This aqueous solution is suitable for the further oxidation by $NaIO_4$ ; it is not necessary to isolate the product (4,6-O-benzylidene-D-galactose).

An exemplary embodiment of this procedure is described in detail in Example 1, below. The process has also been carried out successfully using p-methoxybenzaldehyde in place of benzaldehyde.

B. Oxidative Cleavage of (2)

In the procedure of Schmidt and Zimmerman, isolated (2) was oxidized in aqueous solution by addition of solid $NaIO_4$ in the presence of phosphate buffer (pH=7.0–7.6). The product, 2,4-O-benzylidene-D-threose (3), was isolated by evaporation of resulting aqueous solution to dryness and extraction of the solid residue with THF, a very prolonged operation.

As stated above, in the present procedure, the aqueous solution of (2) from the previous step is oxidized directly, without isolation of (2). The solution thus obtained is concentrated to about one third of its initial volume and then extracted with dichloromethane ($CH_2Cl_2$). Other organic solvents such as n-butanol or methyl ethyl ketone may also be used. The organic solution is rapidly dried by filtering through a short silica/$MgSO_4$ (or silica/$Na_2SO_4$) column. Evaporation of the solvent gave pure (3) as a white fragile foam that was easily broken up to a fine powder.

An alternative and possibly more convenient method of isolating (3) from the reaction mixture employs salting out with $Na_2SO_4$ (rather than concentrating the solution) and then extracting with $CH_2Cl_2$. This method would avoid prolonged concentration of the aqueous solution of (3), but larger amounts of $CH_2Cl_2$ would be necessary in this case due to the high solubility of (3) even in concentrated brines.

An exemplary embodiment of the oxidation procedure is described in Example 2, below.

C. Wittig Alkenation of (3); Preparation of Azide (5)

For these steps, conventional procedures, such as described by Schmidt and Zimmerman, were generally suitable for kilogram scale reaction. The Wittig reaction gave a high trans selectivity (approx. 97% by NMR) and yielded about 4 kg of olefin (4) from 4 kg of (3). Wittig reagents having alkyl components of different lengths may be used to prepare various sphingosine analogs.

The Wittig reagent is typically of the form $(Ar)_3P=CHR$, where Ar is aryl and R is a $C_4$–$C_{26}$ branched or unbranched alkyl or alkenyl chain. Ar is typically phenyl but may also include $C_1$–$C_4$ alkyl substituted phenyl or naphthyl. Wittig-type reactions in which Ar is other substituted phenyl, such as nitrophenyl or carboxyphenyl, have also been described (Schiemenz et al.). Phosphorus ylids suitable for use in the reaction can also be prepared from trialkylphosphines and trialkylphosphonates (Wittig-Horner reaction), according to methods well known in the art. However, triarylphosphines are generally preferred.

Triflatation and azidolysis reactions were carried out according to known methods, using sodium trifluoromethyl sulfonate and sodium azide, respectively, to give 1,3-O-benzylidene-azidosphingosine (5).

D. Deprotection Reactions

Schmidt et al. used azidosphingosine, prepared by HCl- or pTsOH-catalyzed deprotection of (5), as a key intermediate in the synthesis of sphingosine, ceramides, and other sphingolipids. These deprotection conditions, however, present disadvantages which become more pronounced in medium (ca. 50 g) to large scale (1 kg or more) production. The deprotection is incomplete even after extended reaction (12–78 hours) at room temperature, and the reaction mixture contains an appreciable amount of starting material and by-products. Heating the $CH_2Cl_2$/MeOH medium or employing THF/HCl leads to degradation of the product. (Although Schmidt et al., 1986, reported that the method was "also successful in larger scale preparations", this observation referred to a 20 g scale synthesis.)

In addition, use of sphingosine (7) as a starting material in ceramide synthesis generally requires protection of the OH groups or, alternatively, use of more selective and accordingly more expensive acylating agents. Otherwise, partial acylation of the OH groups occurs, requiring the time consuming purification procedures.

For these reasons, 1,3-O-benzylidene sphingosine (6), prepared by reduction of (5) prior to deprotection, was used as the key intermediate in the present process (FIGS. 2 and 3). It was synthesized by $NaBH_4$ reduction of (5) in refluxing isopropanol (FIG. 2), as described in Example 3, below, or alternatively, by $LiAlH_4$ reduction in ether at room temperature. This product was then used for the synthesis of D-erythro-sphingosine (7), ceramides (9), D-erythro-dihydrosphingosine (14), N,N-dimethylsphingosine (11), and N,N,N-trimethylsphingosine (13) (FIGS. 2 and 3).

The procedure used for deprotection (FIGS. 2 and 3) differed from that of Kiso et al, who used isopropylidene, rather than benzylidene, derivatives. Benzylidene derivatives give substantially better E/Z selectivity in Wittig alkenation than isopropenylidene derivatives. However, benzylidene deprotection under the conditions used by Kiso (acetic acid with small amounts of water) progresses very slowly at 5–50° C. At higher temperatures (60–80° C.), the rate is still unsatisfactory and formation of by-products occurs.

Accordingly, more suitable procedures for deprotection of benzylidene derivatives (6), (8), (10), and (12), using ion exchange resins, were used for the present processes. Exemplary procedures, for conversion of (6) to sphingosine (7), and for deprotection of 1,3-O-benzylidene ceramides (8), are described below in Examples 4 and 5.

FIG. 3 illustrates the N-alkylation of (6), followed by deprotection, to give N,N-dimethyl sphingosine (11) and the N,N,N-trimethyl ammonium salt (13). The alkylations were carried out using formaldehyde/sodium cyanoborohydride and dimethylsulfate/sodium bicarbonate, respectively. Preferably, alkylation is carried out prior to deprotection. As shown in FIG. 2, catalytic hydrogenation of D-erythro sphingosine (7) gave D-erythro dihydrosphingosine (14); this reaction may be carried out before or after deprotection. All of the reactions illustrated in FIGS. 2–3 have been carried out successfully on a large scale.

The following examples illustrate but are not intended in any way to limit the invention.

EXAMPLES

Example 1

Preparation of 4,6-O-benzylidene-D-galactose (2) (BG)

A portion of $ZnCl_2$ (23 kg, 171 mol) was placed into a reactor, taking measures to exclude moisture. Benzaldehyde (70 L, 680 mol) was poured into the reactor, and the mixture was stirred for about 30 minutes using a powerful mechanical stirrer. After initial dissolution of zinc chloride, a thick slurry of a benzaldehyde-$ZnCl_2$ complex forms. Anhydrous D-galactose (30 kg, 164 mol) and more benzaldehyde (60 L, 570 mol) were added to the warm slurry, and the mixture was allowed to react at RT for 24 hours with vigorous stirring. The precipitate was filtered off and washed portionwise with benzaldehyde (10–15 L total) and then with acetone, to give, after air-drying, 6-7 kg of unreacted D-galactose, probably as the monohydrate. The combined filtrate and benzaldehyde washings were diluted with ether (70 L) and petroleum ether (80 L), and the mixture was extracted with ice-cold water (140 L). The organic layer was washed 3 times with ice water (70 L each time), and the combined aqueous layers were neutralized by rapid addition of a solution of potassium carbonate (38 kg of anhydrous carbonate in approximately 45–50 L of water). The resulting thick suspension of zinc salts was filtered, and the precipitate was washed thoroughly with water until 500–600 L of filtrate were collected. After extraction with chloroform (70 L) and with petroleum ether (70 L), the filtrate, containing 4,6-O-benzylidene-D-galactose (2) and a mixture of KCl and $KHCO_3$, and having a pH of about 8.7, was used directly for the following oxidation.

Example 2

Preparation of 2,4-O-benzylidene-D-threose (3)

The solution from Example 1 was placed into a reactor and buffered with a mixture of $K_2HPO_4$ trihydrate (11 kg) and $KH_2PO_4$ (4.5 kg). Sodium periodate (about 39 kg) was introduced into the solution by portions (approximately 0.5 kg) during 5–6 hours with vigorous stirring, maintaining the pH within 7.0–7.5 by periodic addition of 20% aq. KOH. During the addition, the temperature was kept at 20–25° C. by external cooling. The reaction was deemed complete when introduction of further $NaIO_4$ did not lower the pH of the reaction mixture and testing with iodide-starch paper showed an excess of $NaIO_4$ which persisted for 0.5 h. Completion was further verified by TLC (silica gel, toluene-ethanol 3:1).

The reaction suspension was concentrated in vacuo (at ~40° C.), without prior filtering, to approximately 150 L. Dichloromethane (160 L) was added, and the precipitate of inorganic salts was filtered off and washed thoroughly with $CH_2Cl_2$ (additional 70 L). The two-phase filtrate was allowed to separate, and the lower layer ($CH_2Cl_2$ solution of (3)) was passed through a column (D=30 cm) filled with dry $MgSO_4$ (10 cm column), followed by silica gel (30 cm) and another layer of $MgSO_4$ (10 cm). The aqueous layer was extracted 3 times with 70 L portions of dichloromethane, and the extract was passed through the same column. The column was then eluted with 115 L chloroform to wash residual (3) from the silica gel. The combined eluates were concentrated in vacuo to a syrup and diluted with benzene to approximately 90 L. The solution was immediately (to prevent crystallization of (3)) dried in vacuo to give a solid foam. Yields of 2,4-O-benzylidene-D-treose (3) ranged from 12.5 kg to 13.6 kg (about 36–39% from D-galactose).

Example 3

Reduction of 1,3-O-benzylidene azidosphingosine (5)

Azido derivative (5) (100 g, 0.25 mol) was refluxed with 19 g (0.5 mol) $NaBH_4$ in 1 L of 2-propanol for 48 hours. The reaction mixture was cooled to room temperature, filtered, and treated with acetone to decompose the unreacted borohydride. The resulting solution was then evaporated to dryness under reduced pressure. The solid residue was extracted with 3×500 ml of boiling petroleum ether (60–80°) or hexane, and the combined extracts were filtered and evaporated. The residue was recrystallized from $EtOH/H_2O$ to give 70 g (75%) of derivative (6): mp 51–52° C.; $[\alpha]_D$+38.4 (c=0.6,$CHCl_3$).

Example 4

Deprotection of 1,3-O-benzylidene-D-erythro-sphingosine (6)

A 50 g portion (0.129 mole) of 1,3-O-benzylidene-D-erythro-sphingosine (6) was dissolved in 1.5 L of 90% MeOH and passed through a column filled with ~400 ml of a strongly acidic ion exchange resin such as Dowex™-50 or Amberlite™. The column was then slowly eluted with 90% MeOH up to disappearance of benzaldehyde in the eluate (determined by TLC, HPLC or UV). The reaction is usually complete within 20–30 minutes at room temperature. The final product was then eluted with a 9:1 mixture of MeOH/conc. $NH_4OH$. Dichloromethane and water,were then added to the eluate to give a ratio of $CH_2Cl_2/MeOH/H_2O$ 8:4:3. The organic (lower) phase was separated, dried over $Na_2SO_4$, and evaporated to gives ~36 g (94%) of 97–98% pure D-erythro-sphingosine, mp 73–76° C.; $^1H$ NMR spectrum in accordance with literature.

Example 5

Preparation and deprotection of 1,3-O-benzylidene-ceramides (8) with Different Fatty Acid Chains Acylation of 1,3-O-benzylidene-D-erythro-sphingosine (6) was carried out using a variety of carboxylic acids ($C_2$–$C_{26}$), catalyzed by DCC, in $CH_2Cl_2$, or acid chlorides in $CH_2Cl_2$, according to known procedures. Yields of acyl derivatives (8) were 92–98%.

Protected ceramide (8) (~0.1 mol) was dissolved in 1.5–3.0 L (depending on the solubility of the ceramide) acetic acid at 60–70° C. Then ~200 g of strongly acidic ion exchange resin were added with stirring, followed by 90% MeOH (about 15–20% of the total volume). The reaction mixture was stirred at 60–70° C. for 3–8 hours until deprotection was complete by TLC and rapidly filtered while hot. The filter was washed with 100–200 ml hot acetic acid, and the combined filtrate was allowed to stand overnight at 0–4° C. The precipitate was filtered off, washed with 200 mL cold acetic acid, 1.5–2.0 L water, 500 mL satd. $NaHCO_3$, and 1–1.5 L water. After lyophilization, 70–85% yield of 95% pure material was obtained. For higher purity, the precipitate was dissolved (without lyophilization) in $CHCl_3$ or $CH_2Cl_2$, dried with $Na_2SO_4$ and purified by column chromatography (1–5 % MeOH/$CH_2Cl_2$), giving >99% pure ceramide (9).

Example 6

Preparation of D-erythro-dihydrosphingosine

A 0.67 mole portion of sphingosine or a sphingosine analog, prepared by the above methods, was dissolved in 3 L of absolute methanol, and 10 g of 5% Pd/C were added. Hydrogenation was carried out at room temperature under 1 atm pressure of $H_2$. The reaction mixture was filtered and concentrated by evaporation, and the residue was recrystallized from n-hexane, giving the product in 80–86% yield with 96–98% purity.

While the invention has been described with reference to specific methods and embodiments, it will be appreciated that various modifications may be made without departing from the invention.

It is claimed:

1. A process for the large scale preparation of sphingosine, a sphingosine analog, or a ceramide, comprising the steps of:
   forming a stirred slurry of benzaldehyde and $ZnCl_2$,
   contacting the stirred slurry with D-galactose,
   filtering the resulting mixture to obtain a solid precipitate and a filtrate,
   diluting the filtrate with diethyl ether and a hydrocarbon solvent,
   extracting the resulting mixture with cold water to provide an aqueous extract,
   removing $Zn^{+2}$ from the aqueous extract by treatment with base or an ion exchange resin, to provide an aqueous solution of 4,6-O-benzylidene-D-galactose,
   treating the solution with an oxidizing agent effective to oxidatively cleave said galactose, to produce a hydroxy aldehyde,
   contacting the hydroxy aldehyde with a reagent of the form $(Ar)_2P=CHR$, where Ar is aryl and R is a $C_2$–$C_{24}$ alkyl chain, to produce a hydroxy olefin,
   reacting the hydroxy olefin with a triflating agent, followed by sodium azide, followed by a hydride reducing agent, to produce an amino olefin, and
   deprotecting the amino olefin by contacting the amino olefin with an acidic ion exchange resin, to produce sphingosine or a sphingosine analog.

2. The process of claim 1, for the large scale preparation of a ceramide, further comprising the step of acylating said amino olefin prior to said deprotecting step.

3. The process of claim 2, wherein said acylating employs a $C_2$–$C_{26}$ acylating agent.

4. A process for the large scale preparation of 4,6-O-benzylidene-D-galactose, comprising the steps of:
   forming a stirred slurry of benzaldehyde and $ZnCl_2$,
   contacting the stirred slurry with D-galactose,
   filtering the resulting mixture to obtain a solid precipitate and a filtrate,
   diluting the filtrate with diethyl ether and a hydrocarbon solvent,
   extracting the resulting mixture with cold water to provide an aqueous extract, and
   removing $Zn^{+2}$ from the aqueous extract by treatment with base or an ion exchange resin, to provide an aqueous solution of 4,6-O-benzylidene-D-galactose.

5. A process for the large scale preparation of 2,4-O-benzylidene-D-threose, comprising the steps of:

forming a stirred slurry of benzaldehyde and $ZnCl_2$, contacting the stirred slurry with D-galactose, filtering the resulting mixture to obtain a solid precipitate and a filtrate, diluting the filtrate with diethyl ether and a hydrocarbon solvent, extracting the resulting mixture with cold water to provide an aqueous extract, removing $Zn^{+2}$ from the aqueous extract by treatment with base or an ion exchange resin, to provide an aqueous solution of 4,6-O-benzylidene-D-galactose, and treating the solution with an oxidizing agent effective to oxidatively cleave said galactose.

* * * * *